US005747050A

United States Patent [19]

Tolpa et al.

[11] Patent Number: 5,747,050
[45] Date of Patent: May 5, 1998

[54] PEAT-DERIVED BIOACTIVE PRODUCTS, PHARMACEUTICAL AND COSMETIC COMPOSITIONS CONTAINING SAID PRODUCTS AND PROCESSES FOR PRODUCING SAID PRODUCTS AND COMPOSITIONS

[75] Inventors: Stanislaw Tolpa; Tadeusz Gersz; Stanislawa Ritter; Ryszard Kukla; Malgorzata Skrzyszewska; Stanislaw Tomkow, all of Wroclaw, Poland

[73] Assignee: Torf Establishment, Vaduz, Liechtenstein

[21] Appl. No.: 849,490

[22] Filed: Mar. 11, 1992

[30] Foreign Application Priority Data

| Mar. 16, 1991 | [EP] | European Pat. Off. | 91104098 |
| May 17, 1991 | [PL] | Poland | 290283 |
| Jun. 3, 1991 | [PL] | Poland | 290508 |
| Jun. 3, 1991 | [PL] | Poland | 290509 |
| Jun. 3, 1991 | [PL] | Poland | 290510 |
| Jun. 10, 1991 | [PL] | Poland | 290606 |
| Jun. 10, 1991 | [PL] | Poland | 290607 |
| Jun. 10, 1991 | [PL] | Poland | 290608 |
| Jun. 17, 1991 | [PL] | Poland | 290693 |
| Jun. 17, 1991 | [PL] | Poland | 290694 |
| Jun. 17, 1991 | [PL] | Poland | 290695 |
| Jul. 17, 1991 | [PL] | Poland | 291078 |
| Oct. 26, 1991 | [EP] | European Pat. Off. | 91118269 |

[51] Int. Cl.$^6$ ............................................. A61K 9/00
[52] U.S. Cl. ......................... 424/401; 424/195.1; 424/489
[58] Field of Search ............................. 424/401, 195.1

[56] References Cited

U.S. PATENT DOCUMENTS

| 3,903,267 | 9/1975 | Miler et al. | 424/195.1 |
| 4,272,527 | 6/1981 | Belkevich et al. | 424/195.1 |
| 4,618,496 | 10/1986 | Brasseur | 424/195.1 |

*Primary Examiner*—Amy Hulina
*Attorney, Agent, or Firm*—Ostrolenk, Faber, Gerb & Soffen, LLP

[57] ABSTRACT

The peat-derived bioactive product contains not more than 70%, preferably not more than 60% by weight of inorganic salts, especially of sodium chloride, based on dry solids. It is obtainable by a process wherein a highly concentrated aqueous solution of inorganic salts, especially of sodium chloride containing peat-derived bioactive ingredients is diluted with demineralized water and subjected to reverse osmosis in order to desalinate the solution, inorganic salts being removed, and wherein the resulting solution is concentrated and clarified, and, optionally, in at least one further step, sterilized and/or spray-dried. A pharmaceutical formulation containing a peat-derived bioactive product, in the form of a gel, is prepared by combining a sterile alcoholic herb extract with sterile glycerol, a sterile aqueous solution of previously powdered peat-derived bioactive product and a sterile menthol solution; the resulting mixture is gradually combined with colloidal silica to convert the liquid composition into gel form, the weight ratio of liquid mixture to silica preferably being from 90:10 to 94:6. A cosmetic preparation such as a gel, ointment, balm, shampoo, bath salt lotion etc. contains as active ingredient the instant peat-derived bioactive product in a quantity of 0.01–10% by weight, preferably 0.05–1% by weight, more preferably 0.05–0.1% by weight.

14 Claims, No Drawings

PEAT-DERIVED BIOACTIVE PRODUCTS, PHARMACEUTICAL AND COSMETIC COMPOSITIONS CONTAINING SAID PRODUCTS AND PROCESSES FOR PRODUCING SAID PRODUCTS AND COMPOSITIONS

The present invention relates primarily to novel peat-derived bioactive products and to a process for producing such products. The invention also relates to pharmaceutical and cosmetic compositions containing these products and to processes for preparing pharmaceutical and/or cosmetic formulations containing said peat-derived bioactive products.

It is known to extract peat by various methods using various extraction media and to use such extracts, containing peat-derived bioactive ingredients, for cosmetic and pharmaceutical purposes.

On of these known processes is described in Polish patent specification No. 124110 (Chemical Abstracts 101 (10), 78854e). According to this prior art process, peat-derived bioactive products are obtained by primary and secondary alkaline hydrolysis of an air-dried raw peat material, followed by acidification of the thus obtained hydrolysate and separation of insoluble solid parts with subsequent second alkalization, acidification of the clear liquid phase and elimination of ballast substances by means of alcohol and ether extraction. In said process, the aqueous phase from the organic extraction is a liquid peat-derived bioactive product.

The known liquid product, being a solution of peat-derived active ingredients in a highly concentrated, nearly saturated aqueous solution of sodium chloride, obtained according to the above cited Polish patent specification, is unstable when stored for a long time and, moreover, contains—regarding the biological activity of the composition—a large excess of neutral inorganic substances. As a bulk product, it is hard to handle, store and process.

It is the main object of the present invention to provide a product which is not afflicted with these disadvantages, i.e. a product which is stable and which can easily be formulated into pharmaceutical and veterinary products as well as be introduced, either in solid state or in any suitable solution, into cosmetic preparations.

In particular, with respect to the use of a peat-derived bioactive product for pharmaceutical purposes, i.e. for the production of pharmaceutical compositions, there was a strong need for providing a solid form which would be well suited for this purpose. As previous attempts aiming at concentration of the known aqueous solution of peat-derived bioactive substances and desalination of the same failed to give a positive result due to the occlusion of active ingredients in a crystallising solid phase, causing decrease of biological activity of the composition, it was very hard to find a suitable process for converting the liquid composition into powder form.

Unexpectedly, it was found that a positive result is achievable if, prior to concentration, the liquid composition is first diluted several times, i.e. by water volumes several times the volume of the composition.

Accordingly, the present invention provides a process by which a peat-derived bioactive product, featuring the above advantageous characteristics, is obtainable from a highly concentrated aqueous inorganic salt—especially sodium chloride—solution containing peat-derived bioactive ingredients, by diluting said solution with demineralised water, e.g. distilled water, followed by reverse osmosis, concentration and clarification. A solution so obtained can easily be converted into a sterile and solid product, well suited to the intended purposes, by sterilization and spray-drying. Dilution is preferably effected with quantities of water several times, preferably 5 to 8 times, the quantity of the concentrated solution to be diluted.

The instant process, applied to the processing of a product obtained according to Polish patent specification No. 124110, consists in expelling residual organic solvents from a post-extraction aqueous phase, separating insoluble parts by filtration under reduced pressure through a sintered ceramic material, diluting the permeate with several times the volume of distilled water and subjecting it to desalination by reverse osmosis to separate excessive mineral salts, mainly sodium chloride, as a permeate. Then, the desalinated solution is concentrated, clarified by centrifugation and sterilised by filtration through a membrane filter, e.g. a Millipore® filter. The resulting microbiologically clean solution may optionally be spray-dried. The sterilised product (liquid or solid) may be formulated into a cosmetic pharmaceutical or veterinary composition. Optionally, the concentrated and clarified solution may be used—without sterilisation and spray-drying—in any suitable dilution as a component in numerous cosmetic compositions.

Preferably, in a spray-drying step, the inlet temperature is set to about 180° C., while the outflow temperature is set to about 90° C.

While the process of the present invention is described above in combination with the process according to Polish patent specification No. 124110, its use is not restricted to such combination, but is applicable generally in the context of a process for obtaining a peat-derived bioactive product from a highly concentrated aqueous solution of inorganic salts, especially of sodium chloride, containing peat-derived bioactive ingredients.

The peat-derived bioactive products provided by the present invention do not contain more than 70% by weight, preferably not more than 60% by weight of inorganic salts, especially of sodium chloride. Since a sodium chloride concentration as low as possible would be desired for an optimal product, especially for pharmaceutical applications and such cosmetic applications where higher concentrations are required, i.e. for face care, lower sodium chloride concentrations, such as 55% and even lower, are most preferred, especially when obtainable by the steps of dilution and reverse osmosis.

Where the process is terminated with the concentration and clarification steps, the product is a concentrated (or thickened) solution. "Concentrated peat extract", referred to in this specification, is a dark-brown liquid of a density of 1.02–1.09 g/ml and has a content of dry solids of not less than 5% by weight. The chloride ion content in dry solids, calculated as NaCl, is not higher than 70%, preferably not higher than 60%, and the pH value of a 1% aqueous solution is 5.0–6.5, generally about 6.0. The lack of a further sterilization step may not be detrimental in certain cases, e.g. for certain cosmetic uses of said concentrated peat extract.

On the other hand, the sterilization step will be mandatory, particularly when the product is intended for the preparation of pharmaceutical compositions. Particularly in such a case, the further step of spray-drying is most preferred, if not mandatory. The product resulting after such a spray-drying step is in powder form and thus particularly suited to the preparation of certain pharmaceutical compositions. A most preferred product of this type is the product commercialised under the designation "TOLPA® Torf Preparation", TOLPA® being a registered trade mark of Torf Corporation, ul. Mydlana 2, Wroclaw, Poland. The abbreviation TTP will be used in the course of this specification to designate said product.

The present invention also relates to pharmaceutical compositions containing as active ingredient a peat-derived bioactive product as hereinbefore described, particularly a product which contains not more than 70% by weight, preferably not more than 60% by weight, of inorganic salts, especially sodium chloride, based on dry solids, together with a pharmaceutically acceptable carrier. The peat-derived bioactive product contained in such pharmaceutical compositions is preferably TTP as defined above. The pharmaceutical preparation contains the peat-derived bioactive product and the pharmaceutically acceptable carrier material, preferably in a weight ratio of between about 1:5 and 1:25, and most preferably between 1:9 and 1:19.

The present invention furthermore relates to a process for preparing a pharmaceutical formulation containing a peat-derived bioactive product, in the form of a gel. This process is characterised in that a sterile alcoholic herb extract is combined with sterile glycerol, a sterile aqueous—preferably concentrated—solution of previously powdered peat-derived bioactive product and a sterile menthol solution, and that the resulting mixture is gradually combined with colloidal silica to convert the liquid composition into gel form, the weight ratio of liquid mixture to silica being from 90:10 to 94:6. Preferably TTP is used as the powdered or concentrated peat-derived bioactive product.

The present invention also relates to a process for preparing a pharmaceutical formulation containing a peat-derived bioactive product, in the form of an ointment. This process is characterised in that a sterile herb extract is gradually combined with a sterile solution of powdered peat-derived bioactive product, that the resulting mixture is gelled with the addition of colloidal silica and that the gel thus obtained is triturated with a previously sterilized mixture of fatty components, such as eucerine and petrolatum, preferably with a weight ratio of liquid components to silica of about 30:20 and of gel to fatty composition of between 32:68 and 34:66. Also here, preferably TTP is used as the powdered or concentrated peat-derived bioactive product.

Cosmetic preparations, which may comprise herbal extracts as well as other auxiliary and enriching components, fragrant compositions and carrier materials allowed for cosmetic use, contain the peat-derived bioactive product according to the present invention in an amount of 0.01–10% by weight, preferably 0.05–1.00% by weight, and most preferably 0.05–0.10% by weight.

Carrier materials may be aqueous solutions of alcohols, all types of emulsions, gels, foaming compositions and fatty carriers. Use of one specific carrier selected from the group of the above mentioned substances allows formulation of various types of cosmetic preparations according to the invention, such as tonics, creams, balsams, cleaning milks etc. for daily body care as well as shampoos, hair balms, foaming bath compositions, all with the addition of peat-derived bioactive products.

Peat-derived bioactive products (peat extracts in abbreviated form) stemming from original raw peat material, such as (among others) therapeutic mud, contain well balanced quantities of mineral and organic compounds, such as mineral salts of the following elements: B, Si, Ab, Fe, Mg, Mn, Cu, Sn, Ni, Ca, Ag and Na; organic compounds, such as aminoacids in free form and as salts; polysaccharides, partially degraded/reacted—in the course of hydrolysis—to desoxysaccharides and/or aminosaccharides. Peat, in particular therapeutic mud, is known and recognised as a material of biological plant and microorganism origin; due to its contents of nourishing and stimulating components it has beneficial effects on humans and mammals; therefore, peat-derived bioactive compositions contain the abovementioned substances in proportions characteristic for the living organisms; this is considered to be an explanation of the advantageous effects of cosmetic and pharmaceutical preparations containing peat-derived active products and compositions. Particularly good effects of the new cosmetic compositions are observed when herb extracts are also present in the formulation. Selection of a suitable herb extract is based on a known typical use of such extracts in cosmetics, modifying the activity of preparations and thus enabling the content of cosmetic preparations to be matched with demands and needs of individuals to be treated.

The present invention is better characterised and explained in the following examples.

EXAMPLE 1

Starting with 1000 kg of air-dried raw peat material, following e.g. the known procedure according to Polish patent No. 124110, a solution of peat-derived bioactive ingredients in a saturated aqueous solution of sodium chloride was obtained in a quantity of about 10 liters. The solution was filtered through a sintered ceramic filter under reduced pressure in order to clarify the solution before desalination of the same. The clear solution thus obtained contains about 95% of NaCl in a dry mass. The dry mass constitutes about 32% by weight of the solution. The volume of this clear solution is about 7 liters.

The clear solution is diluted with 5 to 8 times the quantity of distilled water and in diluted form is subjected to a desalination step carried out by using a reverse osmosis technique using a DDS apparatus. Desalination was carried out for 3 to 4 hours, whereby the excess of mineral salts—mainly NaCl—is separated in the form of the permeate. The desalinated composition contained approx. 65–70% of sodium chloride in the solids. The solution thus obtained, of 6–7 liters by volume, was concentrated 4–5 times in a Buechi rotating evaporator, so that a concentrated solution containing approx. 20% of dry mass was obtained. The resulting concentrated solution was clarified using a Biofuga-Heraeus centrifugal apparatus (flow separator) and then sterilised by filtering through a Millipore® filter.

The resulting microbiologically pure solution was spray-dried in an Anhydro dryer with the outflow temperature set at 90° C. and supply inlet temperature set at 180° C. The yield of dried powder was approx. 200 g.

EXAMPLE 2

The product obtained in Example 1 was used for preparing gel and ointment pharmaceutical compositions, containing also herb extracts synergistically improving the therapeutic effect with respect to certain diseases. For example, a gel and ointment against varicose ulcer of the shank was prepared as follows: 20 g of hippocastanaceous extract, 10 g of calendula extract, 60 g of glycerol, 0.1 g of TTP in the form of a powder obtained as described in Example 1 above, 0.1 g of salicylic acid, 1.0 g of distilled water and 8.8 g of Aerosil® (colloidal silica) were used in order to obtain a gel form of the preparation.

Liquid (non-volatile) ingredients were sterilised before use, by means of heating under reflux for two hours. Herb extracts were combined with glycerol and an aqueous solution of TTP and also with menthol, and silica was gradually added to the obtained mixture, under continuous stirring.

Similarly, in order to obtain an ointment composition, the following ingredients were used: 20 g of hippocastanaceous extract, 10 g of calendula extract, 0.1 g of salicylic acid, 0.1 g of TTP in powdered form obtained as described in Example 1 and 2.0 g of Aerosil® (colloidal silica).

As fatty components, a mixture of the following substances was used: 22 g of eucerine and 45.8 g of petrolatum. Herb extracts were sterilised by heating under reflux for approx. 2 hours. Eucerine and petrolatum were similarity sterilised. Liquid ingredients were carefully combined with silica to obtain a gel, which in turn was triturated with sterilised and fatty components cooled down to room temperature. A stable ointment was obtained which did not separate when stored.

The gel and ointment obtained above were simultaneously applied in the treatment of varicose ulcer of the shank. Ulcers were treated with the gel preparation while the surrounding, nonaffected affected skin was treated with ointment. Addition of colloidal silica is believed to be responsible for prompt dessication while the herbal and peat-derived ingredients are believed to be responsible for the curing effect of the preparation. Fatty components helped to keep elastic the crust and the skin. The results obtained were compared with a control group of patients treated in a classic way. Those who received the new treatment were selected from a group of patients suffering from the disease for many months (sometimes years) without noticeable positive effects. Patients treated with compositions according to the invention showed better results—already within the first few weeks—than control patients.

EXAMPLE 3

Products obtained in Example 1 were used to prepare pharmaceutical formulations in the form of tablets, or granules to be placed in capsules.

A sterile peat-derived bioactive composition in powdered form was combined with a carrier in a weight ratio of 1:9. As a carrier, MYVATEX®TL (tradename of Eastman-Kodak), a mixture of lactose and lubricating substances, was used in a weight ratio of 44:1. Lactose of 50 mesh particle size and MYVATEX®TL were finely disintegrated so that approx. 70% of its mass passed through a 100 mesh screen. A part of the resulting mixture of active composition and carrier was formulated into tablets containing 5 mg of active ingredients. The total mass of each tablet was 50 mg. The other part of the same mixture of active composition and a carrier was granulated using q.s. of ethanol (40% by volume). Granules were sieved and ground if necessary and then filled in capsules in such a quantity that each capsule contained 5 mg of active ingredients by using TTP in mixture with a carrier at a ratio of 19:1.

The tablets obtained as above were tested in order to measure the time of their disintegration in an artificial gastric juice at 37° C.±2° C. using Erweka equipment. The artificial gastric juice was prepared as follows: 2.0 g of sodium chloride and 3.2 g of pepsin were dissolved in 7 ml of hydrochloric acid and distilled water was added up to a total volume of 1000 ml. The pH-value of the resulting solution was approx. 1.2. Desintegration time of a tablet, having a diameter of 5.1 mm and a total mass of 0.0498 g, was 6 minutes.

Further examples relate to numerous cosmetic preparations according to the present invention, having different forms composition and being designed for different applications, containing the beneficial addition of bioactive ingredients derived from peat. Among others, preparations such as tonics, balms, creams, milks, shampoos, foaming bath compositions etc. are described.

EXAMPLE 4

A reaction vessel equipped with a stirrer was charged with 150 g of camomile extract obtained by the extraction of camomile inflorescence with a 1:1 ethanol:water solution, as well as 1 g of TTP as described above. 50 g of glycerol were added to the mixture obtained. The three substances were stirred to obtain a uniform mixture. Subsequently, a second mixture as previously formulated, was introduced into the same vessel. It comprised 340 g of a 95:5 ethanol:water solution, 1 g of salicylic acid and 0.5 g of menthol. The two mixtures were combined by stirring to form a uniform solution. Next, 3 g of a fragrant composition TILIANA H4308 were added. TILIANA H4308 is a product of Fabryka Syntetykow Zapachowych Pollena-Aroma (Synthetic Fragrance Works Pollena-Aroma), of Warsaw, Poland. The solution was then brought to a total volume of 1000 ml by adding 454.5 g of distilled water; stirring was continued until a homogeneous mixture was obtained.

In the above procedure, 86% glycerol, menthol and water according to the requirements of Polish Pharmacopea FP IV and ethanol in a concentration of 95% according to the Polish industrial standard BN-75/6193-01 were used.

The concentrated peat extract used was a dark-brown liquid of a density 1.020–1.090 g/ml and a content of dry solids not less than 5%; the pH value of a 1% aqueous solution was 5.0–6.5. Camomile extract was a red-brown liquid of a density of 0.9160–0.9503 g/ml, and ethanol content of 52–56% by volume.

The tonic preparation obtained above is suitable for all kinds of skin. It is a clear liquid without any solids. Its colour is yellow. The pH value is 4.28 and the ethanol content is 45.92% by volume. Total acidity calculated as salicylic acid content was not less than 0.1% by weight, namely 0.23% by weight. The preparation being stored for 12 months did not lose any of the above characteristic features.

EXAMPLE 5

The procedure described in Example 4 above was repeated, the only difference being that instead of camomile extract and the TILIANA H4308 fragrant composition, a marigold flowers extract and a composition FINUS H4625 (also a product of Fabryka Syntetykow Zapachowych Pollena-Aroma) were used in the same way and the same molar and volume ratios. The resulting tonic preparation is suitable for dry and fragile skin. Similarily it was a clear liquid without any solid particles. The pH value was 4.30, total ethanol content was 45.82% by volume and total acidity was 0.27% by weight. When stored, the preparation was unchanged after 12 months like the preparation obtained according to Example 4.

EXAMPLE 6

The procedure of Example 4 was repeated, except that an extract of sage leaves was chosen instead of camomile extract, and the fragrance LELIA 90368 (Pollena-Aroma, Warsaw) was chosen instead of TILIANA H4308. The extract of sage leaves was obtained by extracting dried sage leaves with ethanol at 50° C. and had a brownish colour, a characteristic sage odour and a density of 0.9160 to 0.9503; it contained 52 to 56% of ethanol. The resulting face care agent is particularly suitable for greasy skin. It is a clear and homogeneous liquid having a dark yellow colour; the pH value, the ethanol content and the acidity were comparable with the values of the care agent according to Example 4.

EXAMPLE 7

The following composition proved to be a particularly effective gel for avoiding or treating periodontosis:

| | |
|---|---|
| 24.0 g | camomile extract |
| 3.0 g | sage leaf extract |
| 0.3 g | salicylic acid |
| 0.2 g | menthol |
| 0.1 g | TTP |
| to 100.0 g | commercial gel base |

EXAMPLE 8

The following carefully weighed components were introduced into a reaction vessel of a volume of 2000 ml, equipped with a mechanical stirrer:

270 g of camomile extract obtained by extraction of camomile inflorescence with 50% ethanol; the extract was a red-brown liquid, having a density of 0.9160–0.9503 g/ml and an ethanol content of approx. 55% by volume 50 g of glycerol, 86%, according to the requirements of Polish Pharmacopea FP IV 30 g of a saponaria officinalis extract obtained by extracting saponaria officinalis roots with 70% ethanol; the extract was a red-brown liquid, the density was 0.9630–0.9810 g/ml, and the ethanol content approx. 75% by volume 1.0 g of the inventive concentrated peat extract, being a dark brown liquid having a density of 1.02–1.09 g/ml; not more than 2% chloride ions calculated as sodium chloride; the dry solids content was not less than 5%; the pH value of a 1% water solution of the extract was 6.0.

The ingredients listed above were mixed thoroughly. A previously prepared solution of 1 g of salicylic acid in 260 g of 95% ethanol was added thereto. To the combined solution, 383 g of distilled water and 5 g of fragrant composition TILIANA H3408 were added and stirred until a uniform solution was obtained. The preparation was analysed and stored in retail size bottles of 200 ml volume. The resulting preparation was suitable as a hair care preparation. It was a clear, slightly opalescent liquid, containing approx. 45% by volume of ethanol; the pH value was 4.5; the total acidity calculated as salicylic acid was not less than 0.1% by weight. The preparation is suitable for blonde hair. During 12 months storing the preparation remained unchanged in its features.

EXAMPLE 9

The procedure described in Example 8 was followed except that instead of camomile extract and TILIANA H4308 composition there were used in the same sequence and ratio: horsetail herb extract and the fragrant composition FINUS H4625. Horsetail herb extract was a green-brown liquid of a density of 0.9160–0.9503 g/ml and an ethanol content of 55% by volume.

The resulting preparation was suitable for all kinds of hair. It was a clear and transparent liquid without any solid parts, yellow-brown in colour. pH value, ethanol content, total acidity as well as stability after a 12 months storing period were the same as those of a preparation described in Example 6.

EXAMPLE 10

The procedure as described in Example 8 was repeated with comparable results. The only difference was that, instead of camomile extract and TILIANA H4308 composition, stinging nettle leaves extract and fragrant composition LELIA 90368 (product of the same Fabryka Syntetykow Zapachowych Pollena-Aroma) in the same sequence and ratio were used. The herb extract used was olive-green in colour, had a density of 0.9160–0.9503 g/ml and an ethanol content of approx. 55% by volume. The preparation was suitable for all kinds of hair.

EXAMPLE 11

In general, cosmetic milks are dispersions of fatty substances acting in both chemical and mechanical ways on the skin. In fact, due to a convenient way of application and better interaction of the fluid and the skin, it is very appropriate to use liquid, more specifically emulsion creams. They can easily penetrate to deeper layers of the skin and thus prevent changes of the skin due to age. Cosmetic milks are used mainly to clean a dry and fragile skin. Accordingly, they must not contain any aggressive volatile oils, while frequently they contain suitable herb extracts like camomile extract or wheat germ extract. Addition of peat-derived bioactive products to such cosmetic milks further improves their positive effects. In particular, the new recipe is as follows:

| | |
|---|---|
| TTP | 0.05 g |
| aloe extract | 20.00 g |
| glycerol | 3.00 g |
| eucerine | 2.00 g |
| white paraffin oil | 1.00 g |
| triethylamine | 1.00 g |
| Aerosil ® (colloidal silica) | 4.00 g |

EXAMPLE 12

Improved regenerative results were observed when TTP and carefully selected fatty carriers were used in a classic nourishing and regenerative cream formula. TTP is used in an amount of 0.01–1.00% by weight in combination with a herb extract (selection depends on the type of skin for which the cream is intended) in an amount of at least 0.05–1.00% by weight, antibacterial preparation in an amount of 0.05–1.00% by weight, synthetic fragrant composition in an amount of 0.01–0.05% by weight and a fatty carrier in the form of a water emulsion, constituting 97.00–99.50% by weight of the whole composition. The fatty composition needs to be a good carrier for the active ingredients and to be well accepted by the skin. Preferably, it is an emulsion of (all amounts in % by weight) 35–45 eucerine, 8–14 petrolatum, 2.5–4 olive oil, 6–10 glycerol and 35–40 water. Preferred herb extracts are marigold flower extract, camomile extract, thyme extract and the like. Preferred recipes are as follows:

| 1. | Eucerine | 39.00 parts by weight |
|---|---|---|
| | Petrolatum | 11.50 parts by weight |
| | Olive oil | 3.13 parts by weight |
| | Glycerol | 7.80 parts by weight |
| | Water | 38.00 parts by weight |
| | NIPAGINA A (anti-bacterial preparation) | 0.40 parts by weight |
| | TTP | 0.05 parts by weight |

-continued

| | | |
|---|---|---|
| Marigold extract | 0.10 | parts by weight |
| Synthetic fragrance | 0.02 | parts by weight |
| total | 100.00 | parts by weight |
| 2. Eucerine | 42.00 | parts by weight |
| Petrolatum | 8.50 | parts by weight |
| Olive Oil | 3.08 | parts by weight |
| Glycerol | 7.90 | parts by weight |
| Water | 38.00 | parts by weight |
| NIPAGINA A (anti-bacterial preparation) | 0.40 | parts by weight |
| TTP | 0.05 | parts by weight |
| Camomile extract | 0.02 | parts by weight |
| Synthetic fragrance | 0.05 | parts by weight |
| total | 100.00 | parts by weight |

EXAMPLE 13

An after-shave preparation contains TTP as a peat extract in an amount of 0.01–1% by weight, herb extracts in an amount of 1–30% by weight, glycerol in an amount of 1–8% by weight, salicylic acid and menthol in aqueous-alcohol solution. Preferred herb extracts are: camomile, marigold, thyme, aloe extract and similar beneficial herb extracts. Addition of glycerol is also beneficial due to its influence on the elasticity of the skin. It speeds up the spreading of the preparation on the face as well as the penetration into the deeper layers of the skin, thus enhancing the beneficial effects of the active peat composition and herb extracts. A preferred recipe is as follows:

| | |
|---|---|
| TTP | 0.10 parts by weight |
| Camomile extract | 15.00 parts by weight |
| Glycerol | 5.00 parts by weight |
| Menthol | 0.10 parts by weight |
| Salicylic acid | 0.10 parts by weight |
| Ethanol (conc. 95%) | 10.00 parts by weight |
| Fragrant composition | 0.30 parts by weight |
| Distilled water | ad 100.00 parts by weight |

EXAMPLE 14

A shampoo composition was prepared according to the following recipe:

| | | |
|---|---|---|
| Fuller's herb extract | 15.00 g | 7.50% by weight |
| Stinging nettle leaves extract | 20.00 g | 10.00% by weight |
| GAMAL SBS-11 (detergent) | 30.00 g | 15.00% by weight |
| GAMAL NO-3 (detergent) | 20.00 g | 10.00% by weight |
| Aseptina | 0.40 g | 0.20% by weight |
| ethanol | 1.60 g | 0.80% by weight |
| BRONOPOL (preservative) | 0.04 g | 0.02% by weight |
| Sodium chloride | 6.00 g | 3.00% by weight |
| Water | 106.96 g | 53.48% by weight |
| total | 200.00 g | 100.00% by weight |

To 92 parts by weight of the above shampoo composition 8 parts by weight of TTP were added to obtain 100 parts by weight of a shampoo according to the invention. Other herb extracts can be used in place of stinging-nettle leaves extract

EXAMPLE 15

The following shampoo composition was prepared:

| | |
|---|---|
| Horse chestnut extract | 13.00 g |
| Marigold extract | 22.00 g |
| GAMAL SBS-11 | 30.00 g |
| GAMAL NO-3 | 20.00 g |
| Aseptina | 0.40 g |
| Ethanol | 1.60 g |
| BRONOPOL | 0.04 g |
| Sodium chloride | 6.00 g |
| Water | 106.96 g |
| total | 200.00 g |

To 95 parts by weight of the above composition, 5 parts by weight of TTP were added to obtain 100 parts by weight of shampoo according to the present invention.

EXAMPLE 16

A tooth paste contains TTP as a concentrated peat extract, in an amount of 0.01–0.10% by weight, etheral oils or their compositions or else fruit essences in an amount of 1–10% by weight, glycerol in an amount of 5–10% by weight, herb extracts in an amount of 0.10–10% by weight and cleaning substances in an amount of 20–35% by weight dispersed in water in an amount of 45–60% by weight, and dyes and whitening components in an amount of 1–2% by weight.

Titanium dioxide may be used as a whitening component; TTP itself may be used as an anti-bacterial additive; sage leaves, camomile or marigold flowers extracts may be used as beneficial preferred herb extracts. The preferred recipe is as follows:

| | |
|---|---|
| Precipitated calcium carbonate | 150.00 g |
| Magnesium carbonate | 60.00 g |
| Glycerol | 70.00 g |
| Herb extract | 5.00 g |
| TTP | 0.50 g |
| Titanium dioxide | 10.00 g |
| Etheral oils (or mint, lemon, etc essence) | 5.00 g |
| Water | 400.00 g |
| Dye | trace |

EXAMPLE 17

Bath salt preparation: In the course of the process for obtaining a peat-derived bioactive product according to the present invention, in particular when converting a liquid form into a powdered one, there is the desalination step in which sodium chloride is separated as a by-product. In said by-product, 95% constitutes sodium chloride, other mineral salts separated are calcium salts, magnesium salts, mainly chlorides and sulfates; these salty products also contain some organic peat-derived low molecular compounds occluded within the crystal structure of these inorganic salts. These organic compounds are components of TTP and are—among others—polysaccharides, aminoacids, fulvic acids and the like. The presence of these components in the salty by-products is beneficial when salt is used as a bath salt, because they may add additional beneficial effects to the standard activity of bath salt. Accordingly this by-product was tested for its chemical and physical properties in the Balneologic Institute in Poznan, Poland, to find out whether it can be used in cosmetic baths. Since the Institute has found no undesired entity in the salt, it was approved for cosmetic use. The preferred recipe is as follows:

| Salt (NaCl) containing occluded TTP | 97.00 g |
|---|---|
| Pine etheral oil or etheral oils composition | 3.00 g |

EXAMPLE 18

A new hair balm contains TTP in an amount of 0.01–1% by weight, herb extracts in an amount of 0.01–10% by weight, anti-electrostatic components in an amount of 3–4% by weight, components preventing excessive drying of hair and skin in an amount of up to 2% by weight, glycerol in an amount or 1–5% by weight, preservative and stabilisers in an amount of 0.05–0.50% by weight and water to 100% by weight.

As an anti-electrostatic component, the present balm contains an alcoholic solution of trimethylamine and ammonium chloride salt, obtained from fatty animal-derived amines; as thickening agent— acting also as stabilizing agent—cosmetic alcohol; as agent preventing excessive dryness of hair and skin—plant oils, acting simultaneously as co-emulsifying agents; and glycerol for easying spreading and penetration of the balm, in particular of its active ingredients TTP and herb extracts. As an acidic enviroment stops multiplication of bacteria, the balm according to the invention contains citric acid or fumaric acid in an amount of 0.1% as well as a preservative known as BRONOPOL and fragrant compositions. The preferred recipe is as follows:

| Alcoholic solution of trimethylamine and ammonium chloride salts | 3–4% by weight |
|---|---|
| Cosmetic alcohols | 3–4% by weight |
| TTP | 0.01–10% by weight |
| Thickened herb extracts | 0.01–10% by weight |
| Glycerol | 1.5% by weight |
| Plant oils | up to 2% by weight |
| Citric or fumaric acid | 0.1% by weight |
| BRONOPOL | 0.1% by weight |
| Fragrant composition | 0.3% by weight |
| Distilled Water | to 100% by weight |

EXAMPLE 19

Cosmetic masks are well known cosmetic preparations serving many different purposes. As therapeutic mud has a known beneficial effect on the skin and body, it was believed that also post-extraction peat obtained in the process of separation of bioactive peat-derived compositions from peat may be used in cosmetic applications. Post-extraction peat contains a solution of active bodies freed in the alkaline hydrolysis process due to extremely high sorptive properties of peat after neutralisation; It was therefore found to be a valuable component of cosmetic masks. To enrich the post-extraction peat with more of the valuable components, natural therapeutic mud and humic acid fractions were added which are present in natural peat and separated in a process for obtaining peat-derived bioactive compositions from the alkaline hydrolysate. Such a composition was tested in the above-mentioned Balneologic Institute and was found suitable for cosmetic use. The preferred recipe is as follows:

| Post-extraction peat | 100.0 g |
|---|---|
| Natural therapeutic mud or peat | 20.0 g |
| Humic acid fraction | 10.0 g |

-continued

| Magnesium carbonate | 10.0 g |
|---|---|
| Zinc oxide | 5.0 g |
| Citric acid or the like | 0.1 g |
| Herb extract or powdered plant material | 5.0 g |
| Distilled water | q.s. |

The following statements and explanations relate to the biological aspect of the products of the present invention, i.e. to the bioactive characteristics and to the compatibility of these products, particularly with a view to their usefulness as pharmaceuticals. The following abbreviations will be used below:

TTP TOLPA® Torf Preparation (trademark of Torf Corporation, Wroclaw, ul. Mydlana 2, Poland)

IFN Interferon exists as a ubiquitous cytokine (tissue hormone). IFN genes are present in all cells. IFN is mainly induced by proteins or glyco-proteins. Substances stimulating the IFN genes for the production of IFN are called inducers. The process of the IFN induction is a highly regulated, sophisticated biochemical process; negative and positive regulatory genes controlling IFN production have been recognized. Small amounts of IFN may be produced spontaneoulsy, without any detectable inducer. Such IFNs are sometimes named "physiological IFNs". IFN exists in nature in three main molecular forms:

| IFN-α | (or leukocyte IFN), |
|---|---|
| IFN-β | (fibroblast IFN), and |
| IFN-γ | (immune IFN). |

IFN-α and IFN-β are type I-IFNs, IFN-γ is the type II-IFN.

The major biological activities of IFNs are antiviral, anti-proliferative (anticancer), and immunomodulatory activities.

Various forms of IFN are produced commercially as the natural and recombinant preparations and are used as drugs for treatment of neoplastic, viral, and several other diseases.

CTL=cytotoxic T lymphocyte.

NK cells=natural killer cell.

IL-1, IL-2 well known interleukins stimulating the proliferation of T cells and other lymphoid cells including B cells;

RPMI 1640 tissue culture medium for the growth of human and other leukocytes (abbreviation of the Roswell Park Memorial Institute, Buffalo);

FCS=fetal calf serum (for assays with leukocytes it has to be pre-tested because it may contain mitogenic substances mimicking the action of interleukins);

EMCV=encephalomyocarditis virus, mouse picorna virus non-pathogenic for humans, it is often used as a challenge virus in the IFN bioassays;

A-549 human adenocarcinoma cell line—used in the IFN bioassays because of its high sensitivity for IFN-α, β, and γ. The line is recommended for such use by the WHO experts on IFN standardization;

MTT 3-[4,5-dimethylthiazol-2-yl]-2,5-diphenyltetrazolium bromide. Reagent used to measure the cell kill or cell growth in several bioassays, using the ELISA scanners (Hansen et al., J. Immunol. Meth. 1989, 119, 203–210);

L929 the mouse cell line, commonly used for assaying mouse IFN and human or mouse TNF;

TNF tumor necrosis factor, cytokine, (relatively small protein, very susceptible to the proteolytic enzymes), produced by monocytes and macrophages (TNF-α known also as cachectin factor causing cachexia in humans and animals);
produced after stimulation with LPS (lipopolysaccharides), viruses, bacteria, and many other agents, very toxic for many virus-infected and neoplastic cells; may also act as a growth factor for fibroblasts. Connected with inflammatory reactions. The related form TNF-β (lymphotoxin) is produced mainly by T cells and some other cells.

PBL peripheral blood leukocytes, normal human leukocytes from healthy blood donors, isolated from "buffy coats" (interphase between red cells and plasma). The responsiveness of PBL from individual donors to various cytokine inducers appears to depend on a genetic set-up of the donors. The high responders and non-responders have been identified. This refers also to the response of PBL to TTP.

The variation in the individual response to inducers of IFN or TNF is more visible when weak inducers are used than when very strong inducers, like viruses, are employed. This is due to the fact that the reaction to weak inducers is of the "all or none" type whereas viruses almost always induce detectable amounts of the cytokines.

Tolerance to inducer:
Called also a hyporeactivity state. Occurs after administration of a single dose of an inducer, e.g. after 20 h of exposure of PBL to an inducer (e.g. virus); the cells stop further production of IFN. The hyporeactivity state lasts usually about seven days. It may be complete or partial. Such reactivity makes the therapeutic application of strong inducers difficult and/or ineffective. Weak IFN inducers either do not induce the hyporeactivity state or the tolerance is small.

Several natural drugs which are extracted from medicinal plants possess immunomodulating properties. TTP appears to be one of them. TTP alters many different immune functions in vitro and in vivo. It initiates balanced immunostimulation, with the capability of non-specifically activating all effector pathways (CD4 helper, weakly CD8 suppressor, CTL, NK cell, and activated macrophage) without cytotoxicity for normal tissues.

TTP has a restorative effect on normal wound healing. Low doses of TTP weakly stimulate IL-1 and IL-2 production. High doses may inhibit the cytokine synthesis.

The respective tests with TTP were carried out by the following methods:
PBL from healthy blood donors were purified by ammonium chloride treatment. The culture medium was RPMI 1640 plus 10% FCS. Approximately $8 \times 10^6$ cells/ml were cultured for 20 h at 37° C., 5% $CO_2$. The antiviral activity of interferon was assayed by EMCV cytopathic effect inhibition in human A549 cells. The MTT method to measure cell kill was also used.

TNF activity was measured in $L_{929}$ cells. In order to define IFN type, the individual IFN samples were treated with different anti-IFN sera for 1 h. Their antiviral activities were compared with non-treated preparations.

The tests indicate TTP stimulates the production of endogenous interferons (IFNS) and tumor necrosis factor (TNF). The response is dose-related.

Seven assayed commercial batches of TTP had comparable biological activity as immunostimulant and the cytokine inducers.

Considerable variation in the response to TTP of leukocytes of the individual blood donors have been observed. PBL of several donors were found to be unresponsive. This may reflect a genetic background.

Potent polyclonal antisera were used, such as anti-IFN-α (Cantell), anti-IFN-α Ly (Namalwa) from K. Fantes, and anti-IFN-γ (Cantell) to neutralize antiviral activity in the supernatants of PBL treated for 20 h with TTP.

The results of the neutralization assays were found to resemble the finger prints of individual blood donors. In other words, proportions of IFN types produced by the individuals varied considerably. The separation of PBL into adherent and non-adherent fractions may potentiate the induced cytokine synthesis.

The hyporeactivity (tolerance) to the induction of IFN by NDV observed 20 h after the initial stimulation of PBL with TTP was either minimal or absent.

All of the seven batches of TTP tested in human PBL as IFN and TNF inducers were found to be active in inducing IFN and/or TNF. The optimal concentration of TTP for IFN induction was 30–100 µg/ml and for TNF induction 100–200 µg/ml. The dose of 200 µg/ml may be subtoxic for PBL, but the synthesis of TNF occurs much faster than that of IFN and faster than the development of moderate cytotoxicity.

The conclusion of the foregoing is the experience that the active principle in TTP pharmaceuticals is an immunoactive fraction of an extract from peat containing organic, primarily bound sugars, aminoacids, uronic acids, humic acid substances and mineral salts including microelements. The $LD_{50}$ in animals is >2400 mg/kg per os.

No mutagenic, genotoxic, embryotoxic, teratogenic or carcinogenic activity of TTP was found. TTP shows no allergenic properties and had no topically irritating activity.

The therapeutic indications include chronic and recurring respiratory tract inflammations and lower leg varicose ulcers, supplementing the treatment of vaginal erosions, and periodontal diseases.

There are clinical observations suggesting that TTP may be useful as an immunomodulator in the supporting therapy of several neoplastic diseases. TTP is used orally (5 mg tablets) or topically.

Of particular relevance and importance appears to be the fact that PBL treated with TTP for 20 h at 37° C. do not develop the hyporeactivity state because they retain the capacity to produce IFN after induction with NDV (Newcastle Disease Virus), a very potent IFN inducer.

The attached Tables 1–24 relate to various biological, e.g. toxicological, hematological and immunological tests. These Tables appear to be self-explanatory and provide for the biologist pertinent information relating to compatibility and biological activity of TTP.

It is worth noting that the concentration of active ingredients in pharmaceuticals, may be higher than in cosmetic compositions due to the following reasons:

Pharmaceuticals are prepared in unit dosages, wherein the content of active ingredients is under strict control; e.g. in tablets, the concentration is adapted to the size of the tablet containing the effective daily dose (or a part of it) of the active ingredient.

The concentration of the active ingredient, e.g. of TTP, in granules with which capsules are filled, preferably is only 5% by weight in order to achieve a sufficient tablet size and to allow an appropriate operation of the capsulating machine.

Another reason is that most pharmaceuticals are administered orally, and the active ingredient is distributed within the whole body. Even though it reaches the skin cells in a very low concentration, the therapeutic effect is remarkable.

Furthermore, cosmetic compositions—contrary to pharmaceuticals—are used in rather uncontrolled quantities, applied locally, with a different penetration rate to different cells.

Some compositions, such as a shampoo which is nearly immediately washed out, have short contact times with the body or hair, and may contain relatively more of the beneficial component; others are applied several times a day and therefore should have a lower content of the active ingredient.

Finally, as in the case of tooth paste, being in contact with the mucous membrane in the mouth, active ingredient penetration is much easier than through the skin, and the concentration of the active ingredient may be lower.

TABLE 1

ACUTE TOXICITY. EFFECT OF ORALLY ADMINISTERED TTP ON THE BIOCHEMICAL PARAMETERS OF BLOOD OF RABBITS

| | Dose | | Examined Parameters | | |
|---|---|---|---|---|---|
| Sex | TTP g/kg | Day of Test | Creatinine (mg %) | Total Protein (g/l) | γ-Globulin (g %) |
| F | 0.0 | 0 | 1.09 ± 0.03 | 65.0 ± 3.49 | 0.53 ± 0.00 |
| | | 7 | 1.03 ± 0.02 | 62.0 ± 0.33 | 0.56 ± 0.01 |
| | 2.0 | 0 | 1.06 ± 0.01 | 58.0 ± 1.46 | 0.50 ± 0.02 |
| | | 7 | 1.14 ± 0.38 | 57.8 ± 1.54 | 0.54 ± 0.01 |
| | 5.0 | 0 | 0.96 ± 0.12 | 70.3 ± 3.52 | 0.55 ± 0.00 |
| | | 7 | 0.94 ± 0.13 | 60.0 ± 2.34 | 0.57 ± 0.00 |
| M | 0.0 | 0 | 0.80 ± 0.11 | 73.8 ± 3.23 | 0.72 ± 0.06 |
| | | 7 | 0.82 ± 0.13 | 75.3 ± 1.02 | 0.79 ± 0.03 |
| | 2.0 | 0 | 0.88 ± 0.05 | 64.6 ± 2.86 | 0.62 ± 0.10 |
| | | 7 | 1.24 ± 0.34 | 64.6 ± 2.03 | 0.67 ± 0.07 |
| | 5.0 | 0 | 0.85 ± 0.03 | 58.5 ± 3.19 | 0.57 ± 0.02 |
| | | 7 | 1.04 ± 0.12 | 57.6 ± 4.68 | 0.56 ± 0.01 |

TABLE 2

ACUTE TOXICITY. EFFECT OF ORALLY ADMINISTERED TTP ON THE ACTIVITY OF THE TRANSAMINASES IN THE SERUM OF RABBITS.

| | Dose | Day | Examined parameters | |
|---|---|---|---|---|
| Sex | TTP g/kg | of Test | Alanine Aminotransferase IU | Asparagine Aminotransferase IU |
| F | 0.0 | 0 | 8.67 ± 1.20 | 22.33 ± 2.60 |
| | | 7 | 9.67 ± 0.33 | 28.67 ± 3.75 |
| | 2.0 | 0 | 10.33 ± 1.76 | 18.33 ± 4.09 |
| | | 7 | 12.33 ± 3.52 | 20.00 ± 5.03 |
| | 5.0 | 0 | 11.33 ± 1.66 | 22.33 ± 3.52 |
| | | 7 | 11.00 ± 3.05 | 20.67 ± 4.66 |
| M | 0.0 | 0 | 10.33 ± 1.76 | 23.00 ± 3.05 |
| | | 7 | 12.00 ± 2.64 | 25.67 ± 4.17 |
| | 2.0 | 0 | 9.00 ± 1.00 | 18.00 ± 1.52 |
| | | 7 | 9.00 ± 0.57 | 20.66 ± 3.52 |
| | 5.0 | 0 | 8.00 ± 1.00 | 18.00 ± 1.00 |
| | | 7 | 11.33 ± 1.66 | 23.00 ± 1.99 |

TABLE 3

ACUTE TOXICITY. EFFECT OF ORALLY ADMINISTERED TTP ON THE HEMATOLOGICAL PARAMETERS OF RABBITS

| | Dose | | Examined parameters | | | |
|---|---|---|---|---|---|---|
| Sex | TTP g/kg | Day of Test | Hemoglobin (mg %) | Hematocrit (%) | Leukocytes $\times 10^{-3}$ | Erythrocytes $\times 10^{-6}$ |
| F | 0.0 | 0 | 12.4 ± 0.44 | 38.3 ± 1.85 | 7.32 ± 0.43 | 5.21 ± 0.20 |
| | | 7 | 11.8 ± 0.63 | 37.7 ± 1.20 | 6.30 ± 0.66 | 5.11 ± 0.11 |
| | 2.0 | 0 | 11.5 ± 0.31 | 36.7 ± 0.88 | 5.69 ± 0.58 | 5.86 ± 0.55 |
| | | 7 | 12.3 ± 0.48 | 38.3 ± 0.66 | 5.74 ± 0.76 | 5.69 ± 0.11 |
| | 5.0 | 0 | 12.3 ± 0.14 | 40.7 ± 2.6 | 7.35 ± 0.99 | 5.42 ± 0.20 |
| | | 7 | 11.6 ± 0.23 | 37.3 ± 0.33 | 8.55 ± 1.79 | 5.08 ± 0.19 |
| M | 0.0 | 0 | 12.0 ± 0.85 | 37.3 ± 1.20 | 11.10 ± 0.63 | 4.53 ± 0.26 |
| | | 7 | 11.9 ± 0.61 | 35.7 ± 1.85 | 10.80 ± 0.94 | 4.54 ± 0.19 |
| | 2.0 | 0 | 12.8 ± 0.26 | 43.7 ± 4.80 | 9.94 ± 2.00 | 4.46 ± 0.65 |
| | | 7 | 11.8 ± 0.39 | 34.7 ± 2.02 | 11.06 ± 1.08 | 5.37 ± 0.56 |
| | 5.0 | 0 | 12.7 ± 0.63 | 38.7 ± 2.40 | 9.52 ± 1.36 | 4.59 ± 0.16 |
| | | 7 | 10.6 ± 1.04 | 4.0 ± 2.08 | 8.87 ± 1.73 | 5.72 ± 0.66 |

TABLE 4

CHRONIC TOXICITY. EFFECT OF ORALLY ADMINISTERED TTP ON THE MASS OF THE ORGANS OF RABBITS

| | Dose of TTP (mg/kg) | | | | | |
|---|---|---|---|---|---|---|
| | 0.0 | 50 | 150 | 0.0 | 50 | 150 |
| Sex | | F | | | M | |
| Organ | Mass of Organ in % of Total Mass | | | | | |
| Lung | 0.72 ± 0.08 | 0.61 ± 0.17 | 0.67 ± 0.0? | 0.56 ± 0.05 | 0.54 ± 0.09 | 0.71 ± 0.14 |

TABLE 4-continued

CHRONIC TOXICITY. EFFECT OF ORALLY ADMINISTERED
TTP ON THE MASS OF THE ORGANS OF RABBITS

| | Dose of TTP (mg/kg) | | | | | |
|---|---|---|---|---|---|---|
| Sex | 0.0 | 50 | 150 | 0.0 | 50 | 150 |
| | | F | | | M | |
| Organ | Mass of Organ in % of Total Mass | | | | | |
| Heart | 0.23 ± 0.01 | 0.22 ± 0.02 | 0.25 ± 0.03 | 0.24 ± 0.02 | 0.23 ± 0.01 | 0.23 ± 0.02 |
| Spleen | 0.057 ± 0.01 | 0.051 ± 0.00 | 0.079 ± 0.02 | 0.05 ± 0.01 | 0.06 ± 0.01 | 0.04 ± 0.01 |
| Liver | 2.85 ± 0.15 | 3.02 ± 0.08 | 3.22 ± 0.37 | 2.82 ± 0.09 | 2.77 ± 0.28 | 3.12 ± 0.06 |
| Kidney | 0.59 ± 0.03 | 0.52 ± 0.02 | 0.50 ± 0.01 | 0.48 ± 0.03 | 0.55 ± 0.01 | 0.49 ± 0.03 |
| Adrenal Gland | 0.016 ± 0.01 | 0.015 ± 0.01 | 0.020 ± 0.01 | 0.013 ± 0.01 | 0.013 ± 0.02 | 0.012 ± 0.0 |
| Ovaries with Uterus | 0.58 ± 0.04 | 0.39 ± 0.02 | 0.60 ± 0.04 | — | — | — |
| Testicles | — | — | — | 0.30 ± 0.01 | 0.32 ± 0.03 | 0.36 ± 0.02 |

TABLE 5

CHRONIC TOXICITY. EFFECT OF ORALLY ADMINISTERED
TTP ON THE HEMATOLOGICAL PARAMETERS OF RABBITS

| | Dose | | Examined parameters | | | |
|---|---|---|---|---|---|---|
| Sex | TTP g/kg | Week of Test | Hemoglobin (mg %) | Hematocrit (%) | Leukocytes ×$10^{-3}$ | Erythrocytes ×$10^{-6}$ |
| M | 0.0 | 0 | 12.2 ± 0.05 | 38.2 ± 1.71 | 9.33 ± 0.79 | 5.10 ± 0.56 |
| | | 7 | 12.3 ± 0.15 | 40.7 ± 0.33 | 9.39 ± 1.18 | 6.34 ± 0.23 |
| | | 6 | 3.0 ± 0.35 | 41.7 ± 1.30 | 9.58 ± 1.12 | 7.32 ± 0.70 |
| | | 12 | 13.5 ± 0.19 | 40.7 ± 0.67 | 11.23 ± 1.10 | 6.30 ± 0.46 |
| M | 50 | 0 | 12.0 ± 0.55 | 35.7 ± 1.82 | 7.52 ± 0.78 | 5.14 ± 0.47 |
| | | 3 | — | — | — | — |
| | | 6 | 13.3 ± 0.35 | 41.0 ± 2.10 | 8.08 ± 1.17 | 6.38 ± 0.11 |
| | | 12 | 13.7 ± 0.11 | 39.3 ± 0.94 | 9.36 ± 1.01 | 6.19 ± 0.19 |
| M | 150 | 0 | 14.20 ± 0.21 | 36.7 ± 1.81 | 8.19 ± 0.16 | 5.34 ± 0.16 |
| | | 3 | 11.05 ± 0.26 | 38.5 ± 1.53 | 8.83 ± 0.78 | 5.68 ± 0.40 |
| | | 6 | 12.40 ± 0.63 | 37.3 ± 1.45 | 8.18 ± 0.06 | 6.84 ± 0.10 |
| | | 12 | 13.70 ± 0.32 | 39.0 ± 0.68 | 8.24 ± 0.04 | 6.54 ± 0.54 |
| F | 0.0 | 0 | 12.6 ± 0.27 | 40.2 ± 0.83 | 7.07 ± 1.16 | 5.63 ± 0.17 |
| | | 3 | 12.1 ± 0.23 | 39.8 ± 0.72 | 8.16 ± 1.01 | 5.74 ± 0.12 |
| | | 6 | 12.4 ± 0.86 | 42.3 ± 1.20 | 9.78 ± 1.69 | 5.86 ± 0.24 |
| | | 12 | 12.5 ± 0.87 | 37.7 ± 2.18 | 10.90 ± 2.16 | 4.60 ± 0.29 |
| F | 50 | 0 | 13.2 ± 1.20 | 35.0 ± 1.70 | 7.44 ± 0.98 | 5.47 ± 0.60 |
| | | 3 | — | — | — | — |
| | | 6 | 13.0 ± 0.55 | 39.3 ± 1.20 | 7.25 ± 0.96 | 7.08 ± 0.94 |
| | | 12 | 12.8 ± 0.21 | 37.7 ± 4.33 | 9.31 ± 0.35 | 6.02 ± 0.32 |
| F | 150 | 0 | 15.2 ± 1.15 | 38.3 ± 1.40 | 8.50 ± 0.54 | 6.09 ± 0.08 |
| | | 3 | 13.1 ± 1.10 | 47.0 ± 2.80 | 8.10 ± 0.76 | 5.85 ± 0.57 |
| | | 6 | 12.5 ± 0.82 | 41.0 ± 1.15 | 6.85 ± 0.31 | 5.61 ± 0.30 |
| | | 12 | 13.1 ± 0.70 | 41.0 ± 1.00 | 8.15 ± 1.68 | 5.92 ± 0.13 |

TABLE 6

EFFECT OF TTP ON THE PHAGOCYTIC ACTIVITY OF NEUTROPHILS IN THE PERIPHERAL BLOOD OF RABBITS

| Group | n | Neutrophiles (1000/1 mm$^3$) | | | % Neutrophiles NBT+ | | | Phagocytic Activity L.H | | | Phagocytic Activity L.W | | |
|---|---|---|---|---|---|---|---|---|---|---|---|---|---|
| | | 0 | 3 | 6 | 0 | 3 | 6 | 0 | 3 | 6 | 0 | 3 | 6 |
| Control 1 ml PBS i.v. | 6 | 1.9 ± 0.9 | 2.3 ± 1.1 | 2.4 ± 0.4 | 14.3 ± 4.6 | 15.1 ± 4.6 | 17.6 ± 3.0 | 54.5 ± 9.4 | 60.6 ± 4.8 | 59.8 ± 6.8 | 7.53 ± 0.77 | 7.53 ± 0.86 | 7.61 ± 0.4 |
| TTP (Test 1) 5 mg/kg i.v. | 15 | 2.0 ± 0.9 | *o 1.2 ± 0.7 | 1.7 ± 7.1 | 18.4 ± 7.1 | *o 26.8 ± 6.7 | *o 27.2 ± 7.0 | 59.2 ± 6.7 | * 69.3 ± 7.0 | * 74.9 ± 7.8 | 8.75 ± 1.18 | * 10.3 ± 1.25 | 9.88 ± 1.0 |
| TTP (Test 2) 5 mg/kg i.v. | 8 | 2.8 ± 0.8 | *o 1.6 ± 0.6 | *o 1.6 ± 1.0 | 15.5 ± 4.9 | *o 22.1 ± 7.0 | *o 26.5 ± 9.1 | 63.0 ± 7.0 | 69.5 ± 7.1 | *o 76.5 ± 8.9 | 7.76 ± 0.83 | 8.52 ± 1.04 | 8.56 ± 1.0 | n Number of Test Animals
PBS phosphate buffer solution
0 Before the administration of TTP
3 3 days after the administration of TTP
6 6 days after the administration of TTP
*Statistically significant variation at p < 0.05 in relation to the value before administration of TTP
o Statistically significant variation at p < 0.05 in comparison to the control group

TABLE 7

EFFECT OF TTP ON THE NUMBER OF LYMPHOCYTES AND ON THE PERCENTAGE OF THE T-LYMPHOCYTES (E-ROSETTES) AND OF THE B-LYMPHOCYTES (EAC-ROSETTES) IN THE PERIPHERAL BLOOD OF RABBITS.

| Group | n | Lymphocytes ×10$^{-3}$/mm$^3$ | | % E-Rosettes | | % EAC-Rosettes | |
|---|---|---|---|---|---|---|---|
| | | 0 | 6 | 0 | 6 | 0 | 6 |
| Control 1 ml PBS | 6 | 6.6 ± 2.0 | 6.0 ± 1.9 | 19.0 ± 5.7 | 20.1 ± 5.5 | 42.1 ± 6.3 | 42.3 ± 2.05 |
| TTP (Test 1) 5 mg/kg i.v. | 15 | 6.6 ± 1.5 | 5.4 ± 1.4 | 19.2 ± 4.1 | *o 27.1 ± 3.2 | 43.7 ± 2.6 | 47.7 ± 4.9 |
| TTP (Test 2) 5 mg/kg i.v. | 8 | 6.0 ± 1.0 | 6.8 ± 0.6 | 17.0 ± 1.9 | *o 24.8 ± 2.9 | 41.6 ± 1.3 | 41.0 ± 2.1 | n Number of Test Animals
PBS phosphate buffer solution

0 Before the administration of TTP
6 6 days after the administration of TTP
*Statistically significant variation at p < 0.05 in relation to the value before administration of TTP
o Statistically significant variation at p < 0.05 in comparison to the control group

TABLE 8

NUMBER OF SPLENOCYTES AFTER LONG-TERM THERAPY WITH TTP

| Time of TTP Doses in Weeks | Control | | TTP 10 mg/kg · day n = 10 PFC/10$^6$ Splenocytes | | TTP 50 mg/kg · day n = 10 | |
|---|---|---|---|---|---|---|
| | 4th Day | 7th Day | 4th Day | 7th Day | 4th Day | 7th Day |
| 3 | 367 ± 157 | 156 ± 41 | 1120 ± 328* | 336 ± 240* | 772 ± 236* | 151 ± 57 |
| 5 | 572 ± 134 | 138 ± 47 | 1528 ± 346* | 292 ± 62* | 1239 ± 280* | 232 ± 90 |
| 7 | 518 ± 45 | 133 ± 40 | 699 ± 136* | 159 ± 44 | 722 ± 258* | 141 ± 63 |
| 9 | 466 ± 185 | 175 ± 75 | 395 ± 94 | 132 ± 36 | 412 ± 138 | 167 ± 62 |
| 12 | 287 ± 18 | 153 ± 30 | 287 ± 131 | 156 ± 39 | 376 ± 130 | 167 ± 69 |

*Statistically significant variation at p < 0.05 in comparison to the control group

TABLE 9

CONCENTRATION OF THE ANTI-SRBC (19S + 7S) ANTIBODIES AT LONG-TERM THERAPY WITH TTP

| Time of TTP Doses in Weeks | Control | | TTP 10 mg/kg · day n = 10 | | TTP 50 mg/kg · day n = 10 | |
|---|---|---|---|---|---|---|
| | \multicolumn{6}{c}{Hemagglutinin, $-\log_2$ of Titer} | | | | | |
| | 4th Day | 7th Day | 4th Day | 7th Day | 4th Day | 7th Day |
| 3 | 3.75 ± 1.78 | 7.12 ± 1.36 | 8.80 ± 0.97* | 9.20 ± 1.46* | 8.20 ± 0.40* | 6.90 ± 1.37 |
| 5 | 5.82 ± 1.40 | 6.50 ± 1.00 | 7.70 ± 0.84* | 9.10 ± 2.02* | 7.70 ± 0.64* | 9.33 ± 2.90* |
| 7 | 3.60 ± 0.48 | 5.20 ± 0.74 | 4.40 ± 1.11* | 4.10 ± 0.83* | 3.50 ± 0.83* | 3.55 ± 1.21 |
| 9 | 3.20 ± 1.40 | 4.66 ± 1.24 | 3.50 ± 1.28 | 4.00 ± 0.81 | 2.90 ± 1.22 | 6.33 ± 1.52 |
| 12 | 4.80 ± 0.74 | 4.40 ± 1.01 | 5.11 ± 1.09 | 5.50 ± 1.51 | 5.11 ± 1.19 | 6.10 ± 1.74 |

*Statistically significant variation at $p < 0.05$ in comparison to the control group

TABLE 10

CONCENTRATION OF THE ANTI-SRBC (7S) ANTIBODIES AT LONG-TERM THERAPY WITH TTP

| Time of TTP Doses in Weeks | Control | | TTP 10 mg/k n = 10 | | TTP 50 mg/kg n = 10 | |
|---|---|---|---|---|---|---|
| | \multicolumn{6}{c}{Hemagglutinin, $-\log_2$ of Titer} | | | | | |
| | 4th Day | 7th Day | 4th Day | 7th Day | 4th Day | 7th Day |
| 3 | 1.75 ± 0.60 | 6.37 ± 0.85 | 3.20 ± 0.87* | 5.90 ± 1.70 | 3.80 ± 0.87* | 4.90 ± 0.74* |
| 5 | 2.50 ± 0.70 | 6.12 ± 1.16 | 2.20 ± 0.97 | 5.70 ± 1.10 | 2.30 ± 1.41 | 5.33 ± 0.74* |
| 7 | 1.00 ± 0.89 | 3.80 ± 1.09 | 0.60 ± 0.80 | 2.50 ± 1.11* | 0.55 ± 0.83 | 2.55 ± 0.68* |
| 9 | 0.40 ± 0.48 | 3.66 ± 1.24 | 0.30 ± 0.64 | 3.25 ± 0.96 | 0.00 | 4.33 ± 1.24 |
| 12 | 0.80 ± 0.97 | 3.80 ± 0.76 | 1.11 ± 0.99 | 4.40 ± 1.35 | 1.55 ± 1.49 | 4.30 ± 1.26 |

*Statistically significant variation at $p < 0.05$ in comparison to the control group

TABLE 11

IMMUNOMODULATORY EFFECT OF TTP (±SD)

| Dose TTP mg/kg | n | PFC/$10^6$ Splenocytes 4th Day | % E-Rosettes 4th Day | Hemagglutinin* Type 19S + 7S 4th Day | Hemagglutinin* Type 7S 7th Day |
|---|---|---|---|---|---|
| Control | 30 | 469 ± 111 | 13.6 ± 3.2 | 5.4 ± 1.1 | 8.2 ± 1.8 |
| | | x | | x | |
| 0.5 | 10 | 997 ± 139 | 15.6 ± 1.4 | 6.8 ± 1.0 | 8.4 ± 1.1 |
| | | x | x | x | x |
| 2.5 | 10 | 839 ± 177 | 20.3 ± 4.1 | 6.9 ± 1.0 | 9.7 ± 1.4 |
| | | x | x | x | x |
| 5.0 | 10 | 746 ± 129 | 23.2 ± 4.7 | 7.2 ± 0.6 | 9.8 ± 1.4 |
| | | x | x | x | x |
| 10.0 | 10 | 795 ± 129 | 18.4 ± 4.0 | 8.3 ± 1.8 | 10.4 ± 1.1 |
| | | x | | | x |
| 25.0 | 10 | 560 ± 145 | 16.3 ± 2.5 | 6.1 ± 1.1 | 9.3 ± 1.1 |
| 50.0 | 10 | 400 ± 57 | 14.7 ± 4.0 | 5.3 ± 1.0 | 6.7 ± 1.9 |
| | | x | x | | |
| 100.0 | 10 | 375 ± 67 | 11.3 ± 2.2 | 5.1 ± 0.8 | 5.7 ± 1.6 |
| | | x | x | | x |
| 250.0 | 10 | 305 ± 67 | 9.5 ± 2.0 | 4.8 ± 1.1 | 5.3 ± 1.7 | x Statistically significant variation at total comparison 0.05
\* $-\log_2$ of titer

TABLE 12

TTP ADMINISTERED DAILY IN 3 DOSES

| | | | 4th Day After Immunization with SRBC | | 10th Day After Immunization with SRBC | |
|---|---|---|---|---|---|---|
| Dose TTP | n | % E-Rosettes | PFC/$10^6$ Splenocytes | Hemagglutinin $-\log_2$ of titer | | Hemagglutinin $-\log_2$ of titer | |
| | | | | 19S + 7S | 7S | 19S + 7S | 7S |
| Control I | 15 | 13.7 ± 3.0 | 469 ± 125 | 5.7 ± 1.3 | 0.8 ± 1.0 | 9.8 ± 1.3 | 8.4 ± 1.6 |
| Control I | 15 | 15.3 ± 4.0 | 579 ± 143 | 6.1 ± 1.1 | 0.6 ± 0.9 | 9.0 ± 1.7 | 8.6 ± 1.8 |
| 2.5 mg/kg 1 × 0.3 ml | 15 | 19.4* ± 3.9 | 864* ± 190 | 7.4* ± 1.1 | 1.1 ± 1.1 | 10.4* ± 1.6 | 9.6* ± 1.2 |
| 2.5 mg/kg 3 × 0.1 ml | 15 | 19.0* ± 5.0 | 769* ± 132 | 7.1* ± 0.8 | 0.5 ± 0.8 | 9.5 ± 1.0 | 9.0 ± 2.0 |
| 10 mg/kg 1 × 0.3 ml | 15 | 19.3* ± 4.1 | 795* ± 102 | 7.0* ± 0.7 | 0.8 ± 1.0 | 10.4* ± 1.6 | 9.4* ± 1.0 |
| 10 mg/kg 3 × 0.1 ml | 15 | 17.5 ± 3.7 | 656 ± 128 | 7.3* ± 1.4 | 1.3 ± 1.2 | 8.9 ± 1.8 | 8.8 ± 1.5 |

TABLE 13

EFFECT OF TTP ADMINISTERED ORALLY FOR 12 WEEKS ON THE IMMUNOLOGICAL RESPONSE OF MICE IMMUNIZED WITH SRBC

| Weeks | 4th Day After | | | | 10th Day After | | | |
|---|---|---|---|---|---|---|---|---|
| | % E-Rosettes | Spleno-cytes | $-\log_2$ of titer 19S + 7S | 7S | % E-Rosettes | Spleno-cytes | $-\log_2$ of titer 19S + 7S | 7S |
| 3 | 15.2 ± 3.8 | 565 ± 56 | 6.0 ± 0.9 | 1.6 ± 1.3 | 14.7 ± 3.4 | 256 ± 67 | 8.7 ± 1.0 | 7.9 ± 1.0 |
|   | 23.7* ± 7.8 | 1035* ± 177 | 7.5* ± 0.5 | 2.9* ± 0.2 | 23.5* ± 3.7 | 406* ± 88 | 10.4* ± 1.2 | 9.7* ± 1.0 |
| 5 | 13.8 ± 2.4 | 422 ± 63 | 5.1 ± 0.9 | 0  0 | 12.7 ± 2.1 | 209 ± 41 | 7.1 ± 1.4 | 6.7 ± 1.6 |
|   | 23.0* ± 6.1 | 933* ± 248 | 7.6* ± 1.5 | 2.7* ± 1.5 | 20.5* ± 2.7 | 430* ± 86 | 11.0* ± 1.2 | 11.0* ± 1.0 |
| 7 | 12.8 ± 2.9 | 495 ± 85 | 4.6 ± 1.1 | 0.5 ± 0.9 | 14.0 ± 5.1 | 245 ± 48 | 8.8 ± 1.6 | 7.9 ± 1.6 |
|   | 20.5* ± 5.3 | 1120* ± 214 | 7.9* ± 0.6 | 2.1* ± 1.5 | 26.9* ± 7.7 | 437* ± 117 | 11.3* ± 1.0 | 10.3* ± 0.4 |
| 9 | 15.0 ± 2.1 | 531 ± 67 | 6.2 ± 0.8 | 0.5 ± 0.9 | 14.1 ± 2.8 | 294 ± 58 | 8.7 ± 1.5 | 8.4 ± 1.5 |
|   | 18.6* ± 2.8 | 1049* ± 184 | 7.7* ± 0.7 | 1.9 ± 1.2 | 18.2* ± 3.4 | 515* ± 530 | 11.9* ± 0.8 | 10.5* ± 1.0 |
| 12 | 15.0 ± 2.6 | 573 ± 143 | 7.2 ± 1.0 | 1.4 ± 1.2 | 16.5 ± 2.6 | 266 ± 58 | 7.5 ± 1.1 | 7.1 ± 0.8 |
|   | 14.1 ± 2.7 | 770* ± 132 | 7.2 ± 1.4 | 1.7 ± 1.7 | 19.0 ± 4.1 | 294 ± 65 | 11.8* ± 0.4 | 10.6* ± 1.0 |

*Statistically significant variation at p = 0.05 in comparison to the control group. In each group, there were 40 animals.

TABLE 14

INFLUENCE OF THE STORAGE CONDITIONS ON THE ACTIVITY OF TTP IN VIEW OF THE ABILITY OF FORMING E-ROSETTES

| | | | % E-Rosettes | | |
|---|---|---|---|---|---|
| | | | after two months storage | | |
| Dose | n | Starting Activity | Temperature +4° C. | At Room Temperature Light Admitted | At Room Temperature in the Dark |
| Control | 8 | 13.6 ± 2.4 | 12.8 ± 2.3 | 12.8 ± 2.3 | 12.8 ± 2.3 |
| 0.1 mg/kg | 8 | 15.8 ± 1.7 | 16.1 ± 3.04 | 15.1 ± 2.9 | 16.0 ± 5.5 |
| 1 mg/kg | 8 | 18.0 ± 0.8* | 19.8 ± 4.1* | 15.3 ± 2.8 | 19.8 ± 2.7* |
| 10 mg/kg | 8 | 20.4 ± 4.2* | 18.0 ± 4.5* | 16.8 ± 2.4* | 16.9 ± 3.5* |

*Statistically significant variation at α = 0.5 in comparison to the control group

TABLE 15

INFLUENCE OF THE STORAGE CONDITIONS ON THE ACTIVITY OF TTP IN VIEW OF THE NUMBER OF CELLS PRODUCING ANTIBODIES OF THE TYPE 19S

| | | | PFC/10⁶ Splenocytes | | |
|---|---|---|---|---|---|
| | | | after two months storage | | |
| Dose | n | Starting Activity | Temperature +4° C. | At Room Temperature Light Admitted | At Room Temperature in the Dark |
| Control | 8 | 571 ± 69 | 514 ± 128 | 514 ± 128 | 514 ± 128 |
| 0.1 mg/kg | 8 | 747 ± 144 | 1039 ± 326* | 718 ± 135 | 1002 ± 210* |
| 1 mg/kg | 8 | 1204 ± 155* | 1026 ± 314* | 793 ± 186* | 1046 ± 331* |
| 10 mg/kg | 8 | 1075 ± 232* | 1070 ± 249* | 869 ± 160* | 848 ± 137* |

*Statistically significant variation at α = 0.5 in comparison to the control group

TABLE 16

INFLUENCE OF THE STORAGE CONDITIONS ON THE ACTIVITY OF TFP IN VIEW OF INFLUENCING THE FORMATION OF ANTIBODIES OF THE TYPE ANTI-SRBC 19S + 7S

|  |  | Starting Activity | | Temperature +4° C. | | At Room Temperature Light Admitted | | At Room Temperature in the Dark | |
|---|---|---|---|---|---|---|---|---|---|
|  |  | | | after two months storage | | | | | |
| Dose | n | | | | | | | | |
| Day | | 4th | 10th | 4th | 10th | 4th | 10th | 4th | 10th |
| Control | 8 | 5.6 ± 0.9 | 9.8 ± 0.6 | 5.0 ± 1.1 | 9.5 ± 2.1 | 5.0 ± 1.1 | 9.5 ± 2.1 | 5.0 ± 1.1 | 9.6 ± 2.1 |
| 0.1 mg/kg | 8 | 7.4 ± 0.4* | 11.4 ± 1.3* | 7.8 ± 1.0* | 10.5 ± 1.7* | 5.4 ± 0.8 | 10.8 ± 0.7* | 6.5 ± 0.7* | 12.6 ± 2.2* |
| 1 mg/kg | 8 | 6.8 ± 6.3* | 12.2 ± 1.1* | 6.7 ± 0.4* | 13.8 ± 2.1* | 6.2 ± 0.3* | 13.2 ± 0.4* | 6.5 ± 1.3* | 13.1 ± 1.3* |
| 10 mg/kg | 8 | 6.4 ± 1.2 | 11.0 ± 1.4* | 6.2 ± 0.6 | 12.0 ± 2.3* | 4.8 ± 1.3 | 10.6 ± 2.4* | 6.0 ± 0.5 | 13.6 ± 1.3* |

*Statistically significant variation at α = 0.5 in comparison to the control group

TABLE 17

INFLUENCE OF THE STORAGE CONDITIONS ON THE ACTIVITY OF TFP IN VIEW OF INFLUENCING THE FORMATION OF ANTIBODIES OF THE TYPE ANTI-SRBC 7S

|  |  | Starting Activity | | Temperature +4° C. | | At Room Temperature Light Admitted | | At Room Temperature in the Dark | |
|---|---|---|---|---|---|---|---|---|---|
|  |  | | | after two months storage | | | | | |
| Dose | n | | | | | | | | |
| Day | | 4th | 10th | 4th | 10th | 4th | 10th | 4th | 10th |
| Control | 8 | 0.4 ± 0.8 | 9.2 ± 0.7 | 0.3 ± 0.7 | 8.1 ± 1.4 | 0.3 ± 0.7 | 8.1 ± 1.4 | 0.3 ± 0.7 | 8.1 ± 1.4 |
| 0.1 mg/kg | 8 | 0 | 10.8 ± 1.0* | 0.7 ± 0.9 | 9.8 ± 0.9* | 0.8 ± 0.9 | 10.0 ± 0.6* | 0.7 ± 0.9 | 11.3 ± 1.4* |
| 1 mg/kg | 8 | 0.8 ± 0.9 | 10.6 ± 0.4* | 0.3 ± 0.7 | 11.5 ± 1.8* | 0.7 ± 0.9 | 10.3 ± 0.7* | 0.7 ± 0.9 | 11.0 ± 1.0* |
| 10 mg/kg | 8 | 0 | 10.2 ± 1.3* | 0.3 ± 0.7 | 9.8 ± 1.0 | 0.3 ± 0.7 | 10.7 ± 2.0* | 0.7 ± 0.9 | 10.3 ± 0.9* |

*Statistically significant variation at α = 0.5 in comparison to the control group

TABLE 18

HEMATOLOGICAL PARAMETERS FOR HEALTHY VOLUNTEERS BEFORE AND AFTER TWO-WEEK ADMINISTRATIONS OF TFP AT A DOSE OF 1 MG/DAY

|  | Placebo n = 5 | | TFP n = 5 | |
|---|---|---|---|---|
| Parameter | 0 | 14 days | 0 | 14 days |
| Erythrocytes × 10⁶/μl | 4.44 ± 0.46 | 4.32 ± 0.45 | 4.32 ± 0.32 | 4.18 ± 0.32 |
| Hemoglobin g/dl | 12.4 ± 2.5 | 11.9 ± 2.8 | 12.8 ± 0.8 | 11.8 ± 0.6 |
| Hematocrit % | 38.1 ± 6.7 | 38 ± 6.9 | 38.7 ± 2.1 | 38.1 ± 1.6 |
| Leukocytes × 10³/μl | 5.25 ± 0.59 | 5.27 ± 0.8 | 5.23 ± 0.6 | 4.86 ± 0.6 |
| Neutrophils % | 52.6 ± 12 | 57.6 ± 11 | 54.2 ± 2.5 | 55 ± 3.6 |
| Lymphocytes % | 26 ± 7.5 | 30.4 ± 8.3 | 34 ± 4.1 | 32.4 ± 5.3 |
| Thrombocytes × 10³/μl | 220 ± 40.4 | 214 ± 35.8 | 221 ± 38 | 214 ± 39.6 |
| Blood Sediment mm/1 h | 7.6 ± 9 | 5.6 ± 1.9 | 7.8 ± 2.7 | 6.8 ± 3.1 |

TABLE 19

BIOCHEMICAL PARAMETERS FOR HEALTHY VOLUNTEERS BEFORE AND AFTER TWO-WEEK ADMINISTRATIONS OF TFP AT A DOSE OF 1 MG/DAY

|  | Placebo n = 5 | | TFP n = 5 | |
|---|---|---|---|---|
| Parameter | 0 | 14 days | 0 | 14 days |
| Total Protein g/l | 72.8 ± 1.76 | 68.42 ± 3.2 | 73.8 ± 1.92 | 70 ± 5.5 |
| Albumine % | 63.2 ± 2.5 | 63.8 ± 2.3 | 63.6 ± 1.8 | 64.4 ± 2.1 |

TABLE 19-continued

BIOCHEMICAL PARAMETERS FOR HEALTHY VOLUNTEERS BEFORE AND AFTER TWO-WEEK ADMINISTRATIONS OF TTP AT A DOSE OF 1 MG/DAY

| Parameter | Placebo n = 5 | | TTP n = 5 | |
|---|---|---|---|---|
| | 0 | 14 days | 0 | 14 days |
| Globulin α1 % | 3.1 ± 0.4 | 3 ± 0.5 | 2.8 ± 0.5 | 2.8 ± 0.45 |
| Globulin α2 % | 5.95 ± 1.9 | 6.8 ± 1.5 | 6.93 ± 0.9 | 0.69 ± 0.9 |
| Globulin β % | 14.4 ± 2.2 | 14.2 ± 1.5 | 13.3 ± 1.9 | 13.2 ± 1.3 |
| Globulin γ % | 12.2 ± 1.5 | 12.1 ± 1.3 | 13.7 ± 0.9 | 12.3 ± 1 |
| IgG g/l | 10.3 ± 1.1 | 10.2 ± 1 | 11.7 ± 1.6 | 11.1 ± 1.4 |
| IgA g/l | 1.8 ± 0.6 | 1.9 ± 0.5 | 1.8 ± 0.5 | 1.9 ± 0.5 |
| IgM g/l | 1.4 ± 0.3 | 1.4 ± 0.2 | 1.1 ± 0.2 | 1.1 ± 0.4 |
| Complement C3 g/l | 1.1 ± 0.1 | 1.1 ± 0.1 | 1.1 ± 0.2 | 0.2 ± 0.2 |
| Complement C4 g/l | 0.2 ± 0.5 | 9.3 ± 0.04 | 0.2 ± 0.0 | 0.2 ± 0.03 |
| Alanine U/l | 34.2 ± 0.05 | 0.3 ± 0.04 | 30.2 ± 8.2 | 31.2 ± 3.2 |
| Asparagine U/l | 32.8 ± 4.4 | 40.2 ± 6.6 | 30.4 ± 7.1 | 39.6 ± 6.6 |

TABLE 20

COMPARISON OF THE FREQUENCY OF ACUTE INFECTIONS OF THE RESPIRATORY TRACTS DURING THE LAST QUARTERS OF THE YEARS 1989 AND 1990 IN RESPECT OF TWO GROUPS OF PATIENTS TREATED WITH TTP AND PLACEBO RESP. DURING OCTOBER 1990

TTP applied during the 4th quarter 1990

| | n | 4th quarter 1989 (no TTP) average number of infections per patient | 4th quarter 1990 (with TTP) average number of infections per patient | statistical significance "p" |
|---|---|---|---|---|
| Cold | 20 | 4.0 ± 1.3 | 1.0 ± 0.5 | <0.01 |
| Sore throat | 20 | 3.3 ± 1.3 | 0.8 ± 0.6 | <0.01 |
| Fever blisters | 20 | 2.1 ± 2.2 | 0.3 ± 0.4 | <0.01 |
| Cough | 20 | 1.4 ± 1.1 | 0.3 ± 0.6 | <0.01 |
| Bronchitis | 20 | 0.3 ± 0.5 | 0 | |
| Pneumonia | 20 | 0.2 ± 0.9 | 0 | |

Placebo applied during the 4th quarter 1990

| | n | 4th quarter 1989 (no TTP) average number of infections per patient | 4th quarter 1990 (with TTP) average number of infections per patient | statistical evaluation of difference "p" |
|---|---|---|---|---|
| Cold | 20 | 3.9 ± 1.4 | 3.1 ± 1.5 | >0.05 |
| Sore throat | 20 | 2.3 ± 2.0 | 2.6 ± 1.7 | >0.05 |
| Fever blisters | 20 | 2.3 ± 1.8 | 1.7 ± 2.1 | >0.05 |
| Cough | 20 | 1.5 ± 1.5 | 1.9 ± 2.0 | >0.05 |
| Bronchitis | 20 | 0.1 ± 0.3 | 0.1 ± 0.3 | |
| Pneumonia | 20 | 0.1 ± 0.3 | 0.1 ± 0.3 | |

TABLE 21

EFFECT OF INTRADERMAL INJECTION OF BACTERIAL ANTIGENS OR PHA (PHYTOHEMAGGLUTININ) IN PATIENTS TREATED WITH TTP

| Ser. No. | Patient (Initials) | Tuberculin $RT_{23}$ | | Streptolycin 0 | | Staphylococci/ anatoxin | | PHA | | NaCl 0.9% | |
|---|---|---|---|---|---|---|---|---|---|---|---|
| | | pre | 3 | pre | 3 | pre | 3 | pre | 3 | pre | 3 |
| 1. | B.T. | + | + | ± | ± | − | ± | − | − | − | − |
| 2. | P.E. | − | + | + | + | ± | − | − | − | − | − |
| 3. | M.H. | ++ | ++ | ++ | ++ | ± | ± | − | − | − | − |
| 4. | W.H. | − | − | − | + | − | − | − | − | − | − |
| 5. | W.H. | − | ± | − | − | ± | − | − | − | − | − |
| 6. | Z.N. | ++ | ++ | − | − | − | ++ | − | − | − | − |
| 7. | P.J. | − | + | ++ | ++ | + | + | − | − | − | − |
| 8. | S.M. | ++ | ++ | + | + | ± | + | − | − | − | − | pre pretreatment
3 after 3 weeks

TABLE 22

EFFECT OF INTRADERMAL INJECTION OF BACTERIAL ANTIGENS OR PHA IN UNTREATED (PLACEBO) PATIENTS

| Ser. No. | Patient (Initials) | Tuberculin $RT_{23}$ | | Streptolycin 0 | | Staphylococci/ anatoxin | | PHA | | NaCl 0.9% | |
|---|---|---|---|---|---|---|---|---|---|---|---|
| | | pre | 3 | pre | 3 | pre | 3 | pre | 3 | pre | 3 |
| 1. | M.M. | − | − | + | ++ | ± | − | − | − | − | − |
| 2. | O.T. | + | + | − | − | ± | ± | − | − | − | − |
| 3. | O.H. | ++ | +++ | ++ | ++ | ± | − | − | − | − | − |
| 4. | W.J. | − | − | − | ± | − | − | − | − | − | − |
| 5. | K.C. | − | − | + | + | ± | + | − | − | − | − |
| 6. | M.J. | ++ | ++ | ++ | + | − | + | − | − | − | − |
| 7. | B.W. | − | − | + | ++ | − | + | − | − | − | − |
| 8. | K.T. | − | − | + | + | + | + | − | − | − | − | pre pretreatment
3 after 3 weeks

TABLE 23

IMMUNOGLOBULINS IN THE SERUM OF PATIENTS WITH ULCUS CRURIS TREATED WITH TTP

| Test | | | Immunoglobulin in mg % | | | |
|---|---|---|---|---|---|---|
| n | Group | | before Treatment | | after Treatment | |
| 8 | A | 1 IgG | 1732.87 ± 207.52 | 7 IgG | 1732.87 ± 207.52 |
| | | 2 IgA | 304.25 ± 47.50 | 8 IgA | 283.87 ± 44.10 |
| | | 3 IgM | 202.87 ± 71.12 | 9 IgM | 189.75 ± 75.15 |
| 8 | B | 4 IgG | 1924.37 ± 246.25 | 10 IgG | 1972.00 ± 239.33 |
| | | 5 IgA | 296.50 ± 59.84 | 11 IgA | 285.50 ± 56.76 |
| | | 6 IgM | 242.12 ± 56.95 | 12 IgM | 232.87 ± 65.45 |
| Statistical Evaluation of Difference | | 1 vs 7 p > 0.05 | | 4 vs 10 p > 0.05 | |
| | | 2 vs 8 p > 0.05 | | 5 vs 11 p > 0.05 | |
| | | 3 vs 9 p > 0.05 | | 6 vs 12 p > 0.05 | |
| | | 1 vs 4 p > 0.05 | | 7 vs 10 p > 0.05 | |
| | | 2 vs 5 p > 0.05 | | 8 vs 11 p > 0.05 | |
| | | 3 vs 6 p > 0.05 | | 9 vs 12 p > 0.05 | |

We claim:

1. A water soluble peat-derived bioactive product, containing not more than 70% by weight sodium chloride, based on dry mass.

2. A peat-derived bioactive product according to claim 1, containing not more than 60% by weight sodium chloride, based on dry mass.

3. A peat-derived bioactive product according to claim 1 obtained by a process, wherein a highly concentrated aqueous sodium chloride solution containing water soluble peat-derived bioactive ingredients is diluted with demineralized water and subjected to reverse osmosis in order to desalinate the solution, inorganic salts being removed, and wherein the resulting solution is concentrated and clarified.

4. A peat-derived bioactive product according to claim 3, obtained by a process comprising at least one of the further steps of sterilizing and spray-drying said resulting solution.

5. A peat-derived bioactive product according to claim 1 obtained by a process, wherein a highly concentrated aqueous sodium chloride solution containing water soluble peat-derived bioactive ingredients, said solution being obtained by primary and secondary alkaline hydrolysis of air-dried raw peat material, followed by acidification of the hydrolysate, separation of insoluble parts and elimination of ballast substances by extraction with organic solvents, and removal of the residual organic solvents from the post-extraction aqueous phase, is filtered through a sintered ceramic filter under reduced pressure, wherein the thus obtained clear filtrate is diluted with demineralized water and subjected to reverse osmosis in order to desalinate the solution, inorganic salt being removed, and wherein the resulting solution is concentrated and clarified.

6. A peat-derived bioactive product according to claim 6 and obtainable by a process comprising at least one of the further steps of sterilizing and spray-drying said resulting solution.

7. A pharmaceutical composition containing as active ingredient a peat-derived bioactive product according to claim 2.

8. A pharmaceutical composition containing as active ingredient a peat-derived bioactive product according to claim 3.

9. A pharmaceutical composition containing as active ingredient a peat-derived bioactive product according to claim 4.

10. A pharmaceutical composition containing as active ingredient a peat-derived bioactive product as claimed in claim 2, and a pharmaceutically acceptable carrier material in a weight ratio of between about 1:5 and 1:25.

11. A pharmaceutical composition according to claim 10, wherein the weight ratio is between 1:9 and 1:19.

12. A cosmetic preparation containing as active ingredient a peat-derived bioactive product according to in a quantity of 0.01–10% by weight.

13. A cosmetic preparation according to claim 12, wherein the quantity is between 0.05 and 1% by weight.

14. A cosmetic preparation according to claim 12, containing, in addition, at least one herbal extract and at least one fragrant.

* * * * *